United States Patent [19]

Hsiung et al.

[11] 4,391,286

[45] Jul. 5, 1983

[54] HAIR CONDITIONING AND COMPOSITION THEREFOR

[75] Inventors: Du Y. Hsiung, Park Forest; Chester A. Davis, Berwyn; Harold J. Nicholson, Roselle, all of Ill.

[73] Assignee: Helene Curtis Industries, Chicago, Ill.

[21] Appl. No.: 236,127

[22] Filed: Feb. 19, 1981

[51] Int. Cl.$^3$ ............................................. A45D 7/00
[52] U.S. Cl. ........................................... 132/7; 424/72
[58] Field of Search ......................... 132/7; 424/70–72

[56] References Cited

U.S. PATENT DOCUMENTS

| | | | |
|---|---|---|---|
| 3,693,633 | 9/1972 | Kalopissi | 132/7 |
| 3,760,819 | 9/1973 | Vogt | 132/7 |
| 3,957,065 | 5/1976 | Busch | 132/7 |
| 4,038,995 | 8/1977 | Edelberg | 132/7 |
| 4,197,865 | 4/1980 | Jacquet | 132/7 |
| 4,214,596 | 7/1980 | Kaplan | 132/7 |

Primary Examiner—A. J. Heinz
Attorney, Agent, or Firm—Dressler, Goldsmith, Shore, Sutker & Milnamow

[57] ABSTRACT

A hair conditioning composition particularly useful in conjunction with hair waving having a pH value of about 4–9 and containing water having dissolved therein about 0.05–5 weight percent quaternary nitrogen-containing conditioning polymer having a molecular weight of about 10,000–10,000,000, and about 0.5–10 weight percent of a water-soluble disulfide-containing polycarboxylic acid or salt thereof, as well as methods for its use and preparation are disclosed.

16 Claims, No Drawings

HAIR CONDITIONING AND COMPOSITION THEREFOR

DESCRIPTION

1. Technical Field

This invention relates to conditioning hair, and particularly to compositions and processes for selectively conditioning hair whose configuration is to be altered.

2. Background Art

Permanent hair waving is usually carried out by subjecting the hair to reagents containing a free —SH group or thiol. These materials are also called mercaptans. In this treatment, the hair is usually first wound on rollers and then saturated with the thiol. The thiol waving agent acts to break the disulfide bonds within the hair fiber forming thiol groups in the hair protein and disulfide bonds between two thiol waving agent molecules. When a sufficient number of hair disulfide bonds have been broken, the hair is realigned to pair previously unpaired hair protein thiol groups opposite each other. At this point, the hair is rinsed, removing the unreacted thiol waving agent and disulfide reaction product formed from it, and then saturated with an oxidizing agent, or neutralizer, such as hydrogen peroxide or a bromate salt, to reform disulfide bonds between the newly paired hair protein thiols and to give the hair a configuration or wave. This process may be used to add curl or straighten the hair.

Salts of thioglycolic acid, such as ammonium thioglycolate, and thioglycolic acid esters, such as glycerol thioglycolate, are typically utilized as the thiol waving agent. Other thiol-containing reagents such as thiolactic acid, beta-mercaptopropionic acid, beta-mercaptobutyric acid, mercaptosuccinic acid and the like are also known in the art to be effective.

As the above waving process is usually carried out, the hair is wet with water or a disulfide bond breaking agent prior to its being wrapped on the rollers. In some instances, the thiol-containing waving lotion is used as the wetting agent, or prewrap, as it is known in the art. This latter treatment begins the hair disulfide bond breaking process, and hastens the overall process. However, as the hair is difficult to wrap while wearing the gloves normally used with thiol waving agents, beauticians frequently use their bare fingers for this step, and continual contact of the skin with thiol-containing reagents may cause skin irritation to some individuals.

The problems of using bare fingers to wrap hair on rollers after treatment with a disulfide bond-breaking reagent was largely solved by the invention of the co-assigned U.S. Pat. No. 4,214,596 to Kaplan et al. That patent describes the use of a bisulfite ion-containing composition in a prewrap which is mild to skin and non-irritating.

One problem which U.S. Pat. No. 4,214,596 did not solve was the under waving and over waving (under and over processing) which may occur during waving on different parts of a single hair fiber or in different areas of the hair mass due to the physical and chemical condition of the hair itself. For example, hair which has been waved, bleached, or bleached and waved is more porous than is hair which has not undergone these chemical treatments, such as portions of the hair fiber near the root which has grown out since the last bleaching or waving. Similarly, even hair having no previous history of bleaching or waving is more porous near the tip end than near the root end simply because hair near the tip has been brushed more, or has been subjected to more weathering.

As a consequence of these porosity differences, the hair tends to take-up more waving agent in some areas, and less waving agent in others. Over waving or processing tends to occur in the more porous portions of the hair while under waving or processing tends to occur in the less porous areas. These trends are exactly the inverse of what is desired since the hair which usually needs the waving treatment the most gets the least waving, and vice versa.

Aside from changes in porosity, hair which has been bleached and/or waved is also believed to have a different chemical make-up than does virgin, unchemically-treated, hair. In addition, older hair which has been brushed more often tends to have a rougher cuticle or outer layer than does hair which is newer, closer to the scalp, and therefore brushed fewer times. This observed roughness is believed to be due to several factors including: (1) the physical abrasion of portions of the cuticle caused simply by repeated contact with hair brush bristles; and (2) the physical damage done to the tip ends when a brush or comb is pulled through the tips at the end of the brushing or combing stroke.

Conditioning agents for hair have been known in the art for several years. Typically, these conditioning agents are relatively small molecules having a single quaternary nitrogen atom bonded to at least one 8–20 carbon atom chain with the remaining nitrogen bonds being taken up by ethyl, methyl or benzyl groups. These conditioners are used after a shampoo as put-on, rinse-out compositions; put-on, leave-on compositions also being known. At least one commercial waving preparation is said to use a relatively small molecule quaternary conditioning agent in the prewrap composition.

A disadvantage of the relatively small molecule quaternary conditioning agents is that they are substantially washed out of the hair after a single shampoo and therefore do not provide a lasting effect. In addition, the relatively small molecule quaternary conditioners provide little, if any, set control to the hair, and tend to leave the hair limp, with little body.

U.S. Pat. No. 3,912,808 to Sokol teaches the use of a polymeric quaternary nitrogen-containing polymer in a composition used for changing the configuration of hair; i.e., a waving lotion. When such polymeric quaternary nitrogen compounds are used as the conditioning agents, it is known that the hair will remain conditioned through several shampoos. However, use of this conditioning agent in a prewrap can lead to hair which is too slippery to wind on rollers. The smaller quaternary molecule conditioning agents also produce some slipperiness on the hair, but not so much slipperiness as to interfere with manipulating the hair, as during rolling of the hair in a waving process.

Water-soluble dithiopolycarboxylic acids and their salts, such as diammonium dithiodiglycolalte, are known to be useful in waving lotion of hair waving preparations to effect some protection from over waving. However, these disulfides are not known to be useful in prewrap preparations. It is known to use a less soluble ester of such disulfides in a prewrap composition in conjunction with a relatively small molecule, quaternary nitrogen conditioning agent. However, the conditioning effect, if any, of the relatively small molecule quaternary nitrogen compound when used with the less-soluble disulfide ester is, as stated above, substantially lost after shampooing.

It would therefore be beneficial if the over waving protection provided by water-soluble disulfides could be combined with the long lasting conditioning properties of a polymeric quaternary nitrogen-containing conditioning agent without the hair slipperiness which is associated with such polymers. Such a composition could be used as a prewrap and allow the proper winding of the hair on rollers, while imparting its conditioning effect through several shampoos and protecting the hair from over waving.

The difficulties associated with manipulation of slippery hair when the configuration of the hair is to be changed are not unique to hair waving. Rather, the provision of a lasting conditioning effect to hair without undue slipperiness is general to hair configurational change processes, such as water setting, where wet or damp hair is manipulated subsequent to the application of the conditioning composition.

SUMMARY OF THE INVENTION

According to the present invention, a unique hair conditioning composition is prepared. This composition contains water having dissolved therein about 0.05 to about 5 weight percent of a quaternary nitrogen-containing polymer having a molecular weight between about 10,000 and about 10,000,000, and about 0.5 to about 10 weight percent of a water-soluble disulfide-containing polycarboxylic acid or salt thereof. The composition of this invention has a pH value between about 4 and about 9 measured at 80° F. (26.7° C.).

In addition, a process for treating hair whose configuration is to be changed subsequent to the application of a conditioning composition of this invention is disclosed. According to this process, a composition of this invention is applied to the hair, distributed substantially evenly therethrough, and the configuration of the hair thereafter altered while the hair is at least partially damp.

The compositions and processes of this invention possess many advantages and benefits.

One advantage of the compositions and processes of this invention is that the hair is selectively conditioned by absorbing more conditioning agent at porous areas needing conditioning the most, and less conditioner at portions of the hair requiring less conditioning.

Another benefit of the instant compositions and processes when used in waving is that the amount of waving tends to be leveled along the hair shaft by protecting porous areas from over processing while permitting enough waving of less porous portions of the fiber. This allows the beautician or home user added leeway in choice of product strength and treatment duration for hair which is between the porosity extremes of virgin hair and bleached and waved hair.

Yet another advantage of the compositions and processes disclosed herein is that their conditioning and over-waving protection lasts through several shampoo treatments, and thus the compositions may be applied days before waving is performed.

Still another advantage of the present invention is that when a composition is applied prior to changing the hair configuration, the hair is easily wrapped on rollers without the usual slippery feel associated with polymeric quaternary nitrogen conditioning agents. In addition, when used as a permanent wave prewrap, the beautician need not wear gloves during wrapping because the compositions of this invention are not irritating to the hands.

Yet another benefit of the present invention is that the compositions may be used as a put-on, leave-on product or as a put-on, rinse-out product and in either use add a long term conditioning benefit to the hair.

An additional benefit of this invention is that the tensile strength of waved hair treated with its compositions tends to be greater than that for hair which has only been waved, and not treated with the compositions disclosed herein.

Still other benefits and advantages of the instant invention will be apparent to those skilled in the art from the disclosure which follows.

DETAILED DESCRIPTION OF THE INVENTION

The compositions of the present invention are broadly useful for conditioning human hair. These compositions are particularly useful for conditioning hair whose configuration is to be changed subsequent to the application of the conditioning composition since configuration changes typically require manipulation of the hair, and use of the compositions of this invention provides hair which is conditioned but not too slippery to manipulate.

As used herein, changing or altering the configuration of hair is meant to include both straightening and curling processes which are carried out while the hair is wet, or at least damp. Illustrations of hair configuration changing processes include, but are not limited to, hair waving using a thiol-containing reagent and water setting.

Since the problems associated with hair waving typically include those found in other hair configurational change processes, as well as those intrinsic to waving, the discussion hereinbelow will be primarily centered upon the application of the instant invention to hair waving. It should be understood however, that use of the compositions of the present invention is not limited to hair waving processes, and includes use on tinted hair, on bleached and/or previously waved hair, or as a pre-treatment prior to oxidative color or bleaching treatments, or whenever conditioning is desired.

The unique compositions of this invention are prepared by dissolving both a water-soluble, disulfide-containing polycarboxylic acid or salt thereof and a quaternary nitrogen-containing polymer in water. The words "dissolving" and "solution" in their various grammatical forms, are meant herein to include the formation of true solutions as well as the formation of substantially clear, non-settling dispersions. High molecular weight polymers rarely form true solutions in water and tend, at best to form non-settling, substantially clear dispersions. Some lower molecular weight polymers may form true solutions.

The preferred water-soluble disulfide-containing polycarboxylic acids, also called dithiopolycarboxylic acids, useful herein are typically symmetrical in structure on either side of the disulfide bond, although asymmetrical compounds may also be used. These disulfides are typically formed by the oxidation of two molecules of mercapto-monocarboxylic acid. The preferred disulfide-containing polycarboxylic acids of this invention are illustrated by dithiodiglycolic acid, 3,3'-dithiodipropionic acid, cystine, dithiodilactic acid, dithiodisuccinic acid and the like; dithiodiglycolic acid being especially preferred.

The disulfide-containing polycarboxylic acids may be present in the compositions of this invention at about 0.5 to about 10 weight percent of the total composition when it is put on the head. In preferred practice, the water-soluble disulfide-containing polycarboxylic acid is present at about 1 to about 5 weight percent of the total composition.

The dithiopolycarboxylic acids may be added to the water as the free acids and the pH value of the resulting solution thereafter adjusted, if necessary, as discussed hereinafter. Preferably, however, the dithiopolycarboxylic acids are used as their water-soluble salts; the preferred cations being alkali metal ions such as sodium or potassium, or more preferably the ammonium ion. Cosmetically acceptable substituted ammonium ions such as the alkanolammonium ions, illustrated by the monoethanolammonium, di-isopropanolammonium and triethanolammonium ions, are also useful cations. The above described amounts of dithiopolycarboxylic acid in the compositions of this invention are calculated as the acid, rather than as a salt thereof.

A wide variety of water-soluble quaternary nitrogen-containing polymers are useful herein. Broadly, such polymers are useful in the range of about 0.05 to about 5 weight percent of the compositions. Preferably, these polymers are present in the range of about 0.1 to about 2 weight percent, and more preferably these polymers are useful in the range of about 0.1 to about 1 weight percent. The molecular weights of the polymers useful herein are broadly between about 10,000 and about 10,000,000, and preferably between about 100,000 and about 4,000,000, with various useful polymers having a generally more narrow molecular weight range.

The preferred polymeric cationic polymers include those prepared from polydiallyldimethylammonium salts as is described in U.S. Pat. No. 3,288,770 and No. 3,412,091. These polymers may be prepared by polymerizing diallyldimethylammonium chloride or bromide, or other suitable diallyldimethylammonium salts, using a free radical generating polymerization catalyst, such as a peroxide or hydroperoxide, then employing a suitable anion exchange resin. The resulting polymers are polydiallyldimethylammonium salts, such as polydiallyldimethylammonium chloride. The homopolymer so produced has been given the name Quaternium-40 in the *CTFA Cosmetic Ingredient Dictionary* (*CTFA Dictionary*), 2nd ed., 1977, published by the Cosmetic Toiletry and Fragance Association, Inc.

The copolymer formed using acrylamide and a diallyldimethylammonium salt is also useful herein. The *CTFA Dictionary* name for the diallyldimethylammonium salt copolymerized with acrylamide is Quaternium-41.

Both Quaternium-40 and Quaternium-41 are commercially available under the respective designations MERQUAT-100 and MERQUAT-550 from Merck & Company, Inc. The polymer of the product designated MERQUAT-100 is said by the manufacturer to have a molecular weight of about 100,000 to about 1,000,000, while the polymer of the product designated MERQUAT-550 is said by the manufacturer to have a molecular weight of about 1,000,000 to about 10,000,000. MERQUAT-100 is sold as a 40 weight percent aqueous solution of the polymer, and has a Brookfield viscosity at 25° C. in the range of about 8,000–12,000 centipoises (cps). MERQUAT-550 is sold as an 8 weight percent aqueous solution of polymer, and has a Brookfield viscosity at 25° C. in the range of about 7,500–15,000 cps.

Another preferred quaternary nitrogen-containing polymer useful herein is a cationic guar. This material has 3-trimethyl-ammonium-2-hydroxypropyl groups bonded to the mannopyranosyl and galactopyranosyl units which make up the guar chains; chloride ion being the anion usually associated with the polymer. The name adopted by the Cosmetics, Toiletries and Fragances Association for this material, although not appearing in the above *CTFA Dictionary*, is Guar Hydroxypropyltrimonium Chloride. A suitable cationic guar is supplied under the designation COSMEDIA GUAR C 261 by Henkel, Inc., while a similar material is sold under the designation JAGUAR C-13-S by Stein, Hall & Company, Inc.

A copolymer prepared from about 80 weight percent N-vinyl pyrrolidone and about 20 weight percent N,N-dimethyl-aminoethyl methacrylate, quaternized with dimethyl sulfate is also preferred herein. This material is named Quaternium-23 in the *CTFA Dictionary*.

Quaternium-23 is available from GAF Corporation under the designation GAFQUAT-755 and GAFQUAT-734. The polymer designated GAFQUAT-734, has an average molecular weight of less than about 100,000, while that designated GAFQUAT-755 has a molecular weight of greater than 1,000,000.

Yet another preferred polymer useful herein is a copolymer prepared from acrylamide and N,N-dimethylaminoethyl methacrylate, quaternized with dimethyl sulfate. Viscosities of 1 weight percent aqueous solutions of these polymers typically have Brookfield viscosities of about 35 to about 1200 cps.

These copolymers are named in the *CTFA Dictionary* as Quaternium-39, and are available under the designation RETEN from Hercules, Inc. Commercially available polymers include those designated RETEN SPX 1104, SPX 1105 and SPX 1106.

The copolymers designated RETEN SPX 1104, SPX 1105 and SPX 1106 are stated by their manufacturer as being highly cationic, and are reported to have Brookfield viscosities of 35–50 cps, 100–400 cps and 600–800 cps, respectively, for 1 percent by weight solutions in water at 25° C. RETEN SPX 1104 is most preferred of this type of polymer for use herein. Copolymers designated RETEN 210 and 220 having viscosities in the range of about 600 to about 1200 cps, under the above conditions, are also suitable.

The most preferred water-soluble polymer for use herein is a quaternary nitrogen-containing hydroxyethyl cellulose having a backbone chain of anhydroglucose units with pendant substituent groups bearing a full positive charge spaced along the anhydroglucose backbone. The pendant substituent group are spaced about the anhydroglucose units along the chain, thereby making the substituent groups themselves pendant and spaced along the chain. These hydroxyethyl cellulose derivatives contain a plurality of quaternary nitrogen-containing groups with each anhydroglucose unit having from zero to three quaternary nitrogen-containing groups. These materials are typically prepared by reacting hydroxyethyl cellulose with epichlorohydrin followed by reaction with a tertiary amine; the preferred tertiary amine being trimethylamine. The preparation of these quaternary nitrogen-containing polymers is described in U.S. Pat. No. 3,472,840.

These cationic, hydroxyethyl cellulose derivatives are named Quaternium-19 in the *CTFA Dictionary*, and are commercially available under the designation POLYMER JR from the Union Carbide Corporation. The presently available materials include POLYMER JR-125, POLYMER JR-400 and POLYMER JR-30M. The molecular weights of these polymers are reported to be between about 300,000 and about 1,000,000, with polymers of a given designation having narrower average molecular weights. For instance, POLYMER JR-30M is reported to have an average molecular weight between about 700,000 and 1,000,000, while POLYMER JR-125 is reported to have an average molecular weight between about 300,000 and about 400,000, and nearer to 300,000 than to 400,000. A two percent by weight aqueous solution of POLYMER JR-125 is reported to have a Brookfield viscosity at a 30 r.p.m. spindle speed of 75-175 cps (No. 1 spindle), while a one percent solution of POLYMER JR-30M is reported to have a Brookfield viscosity of 1,000-2,500 cps (No. 3 spindle) under the same measurement conditions.

Of these polymers, POLYMER JR-400 is most preferred. A two weight percent aqueous solution of POLYMER JR-400 at 25° C. reportedly has a Brookfield viscosity of 300-500 cps (No. 2 spindle), again at 30 r.p.m. The average molecular weight of POLYMER JR-400 is said to be between about 300,000 and about 400,000, nearer to 400,000 than 300,000, and above that of POLYMER JR-125.

As used, the compositions of this invention suitably have a pH value of from about 4 to about 9. When used generally as a conditioner, the compositions preferably have a pH value of from about 5 to about 8, while when used as a prewrap before a waving process, the pH value is more preferably from about 6.5 to about 8.

The mechanisms by which the composition and process of the instant invention provide their unique and lasting selective conditioning and over waving protection results are not known. While not wishing to be bound by any one set of theories or hypotheses, it is thought, however, that the composite mode of action of the compositions of this invention may be as follows.

First, it is believed that treating hair to be waved with a solution of a dithiopolycarboxylic acid before the thiol-containing waving lotion is applied can allow more of the over-waving protective dithiopolycarboxylic acid, or its salt, to be taken up by the hair than when the dithiopolycarboxylic acid is used in the waving lotion. This is because there can be no competition for binding sites within the hair fiber between the dithiopolycarboxylic acid and the thiol-containing waving agent when the former is applied before the latter.

Second, as the accompanying Example 4 demonstrates, the useful conditioning, quaternary nitrogen-containing polymer binds more to hair with a previous history of bleaching and/or waving than to virgin hair, and it is bleached and/or waved hair which is most susceptible to over waving. Consequently, a further possible mode by which selective protection from over waving is afforded by the compositions of this invention may be due to the formation of a physical barrier to penetration of the hair fiber by the thiol-containing waving agent caused by selective polymer binding to those portions of the hair which have a previous history of bleaching and/or waving or are otherwise relatively porous.

Third, the dithiopolycarboxylic acid or its salts are found to have a synergistic effect on the conditioning caused by the quaternary nitrogen-containing polymer. Thus, while it is known that the polymers useful herein will condition hair, hair treated with the polymer alone tends to be too slippery when wet or damp to wind effectively on rollers. However, it has now been found that when quaternary nitrogen-containing polymers are combined with the dithiopolycarboxylic acid or its salts, as taught herein, the wet or damp hair is still conditioned, but it is not so slippery that it will not wind properly on rollers. The conditioning effect is also found to last through several shampoo treatments. Additionally, hair treated with the compositions of this invention has more body than hair treated with either an equal amount of the quaternary polymer or the dithiopolycarboxylic acid alone. This is shown in Example 3, hereinafter.

In addition to the water, dithiopolycarboxylic acid or salts thereof and quaternary nitrogen-containing polymer, additional ingredients may also be present in the compositions of this invention. These additional ingredients may be selected from preservatives, perfume, one or more surfactants, nonionic surfactants being preferred, colorants, and additional conditioning agents, such as benzalkonium chloride.

An illustration of the use of the conditioning compositions of this invention on hair whose configuration is to be changed is as follows. The hair is usually first shampooed and left wet or damp. It is then treated with a composition of this invention by applying the composition to the hair and distributing the composition substantially evenly therethrough. The configuration of the hair is thereafter altered while the hair is wet or at least partially damp from the application of the conditioning composition. The configuration of the hair can be altered by winding upon rollers, or the like, with no other treatment, or by further treatment with a waving or straightening agent as is known in the art, and then dried.

Additional steps are carried out when hair is to be waved substantially immediately after treatment with the composition of this invention, e.g., while the hair is still at least partially damp after application. In this embodiment, the hair is divided into a plurality of sections and a composition of this invention is applied to a section, distributed substantially evenly therethrough, and the treated section wound on a roller. These steps are then repeated on each of the remaining hair sections until all of the hair to be waved is wound on rollers. Because of the mildness of the compositions of this invention, no gloves need be worn during the wrapping step. The hair is thereafter waved by conventional techniques.

Best Modes For Carrying Out The Invention

Example 1: Prewrap Composition

| | Components | Weight percent of the Composition |
|---|---|---|
| (1) | Water (deionized) | 91.02 |
| (2) | Quaternary Nitrogen-containing Polymer (Note 1) | 0.25 |
| (3) | Dithiopolycarboxlic acid salt (Note 2) | 8.0 |
| (4) | Surfactant (Note 3) | 0.5 |
| (5) | Preservative | 0.115 |
| (6) | Perfume | 0.04 |
| (7) | Ammonium hydroxide (28% NH$_3$) | 0.075 |

-continued

| Components | Weight percent of the Composition |
|---|---|
| | 100.00 |

(Note 1) The most preferred, water-soluble quaternary nitrogen-containing hydroxyethyl cellulose derivative designated POLYMER JR-400, available from Union Carbide Corporation was used. This material has the CTFA Dictionary name Quaternium-19.
(Note 2) Diammonium dithiodiglycolate was used. This material was 27% active expressed as dithiodiglycolic acid, providing the composition with 2.16 weight percent active dithiodiglycolic acid or 2.56 weight percent diammonium dithiodiglycolate.
(Note 3) A nonionic surfactant comprised of a mixture of laurate esters of sorbitol and sorbitol anhydrides, consisting predominantly of the monoester condensed with approximately 20 moles of ethylene oxide was used. This material has a CTFA Dictionary designation of Polysorbate-20.

The prewrap of this Example was prepared by premixing Components 5 and 6 in Component 4 until the mixture was substantially homogeneous. The substantially homogeneous mixture was then admixed with the deionized water (Component 1) which had been heated to a temperature of about 80° F. The resulting aqueous admixture was then stirred for about 15-20 minutes and maintained at a temperature of about 80° F. during the remainder of the preparation. The quaternary nitrogen-containing polymer (Component 2) was then sifted into the aqueous admixture and the resulting composition stirred until the polymer dissolved. Diammonium dithiodiglycolate (Component 3) was thereafter added with stirring until a substantially homogeneous solution was obtained. The pH value of the composition was thereafter adjusted using ammonium hydroxide (Component 7) to between 7.0 and 7.5 at 80° F.

Example 2: Put-on, Leave-on Composition

| Components | Weight Percent of Composition |
|---|---|
| Water (deionized) | 90.8057 |
| Quaternary Nitrogen-containing Polymer (Note 1) | 0.25 |
| Dithiopolycarboxylic acid Salt (Note 2) | 8.0 |
| Surfactant (Note 4) | 0.5 |
| Preservative | 0.115 |
| Perfume | 0.10 |
| Benzalkonium Chloride (50% active) | 0.14 |
| Colorant | 0.0143 |
| Ammonium hydroxide (28% NH$_3$) | 0.075 |
| | 100.00 |

(Note 4) A nonionic surfactant comprised of nonylphenol condensed with an average of 15 moles of ethylene oxide was used.

The composition of this Example was prepared in a manner similar to that of Example 1, and the pH value of several preparations, measured at 80° F. was between 7.3 and 7.7.

The composition of this Example was compared to water on models' heads as a put on-leave on conditioner. All of the models had had permanent waves two weeks to three months prior to this comparison, and some had also had a prior color treatment.

The hair on one side of a hypothetical line drawn from the nose to the nape of a model's neck (half-head) was treated with water while the other half-head was treated with the composition of this Example. After application, the treating composition was combed through the hair, the hair set on rollers and then dried.

Beauticians applying the two compositions noted that the side treated with the conditioner of this Example was easier to comb through and wrap and had a better wet feel; i.e. was smoother than was the half-head treated with water alone. When the hair had dried, the half-head side treated with the composition of this invention had better body, sheen and manageability, less fly-away and a firmer set than the hair of the half-head side treated with water. In addition, no tackiness, greasiness or flaking was observed on the half-head side treated with the composition of this Example.

Example 3: Comparative Properties

Aqueous compositions containing the quaternary nitrogen-containing polymer and dithiopolycarboxylic acid salt of Examples 1 and 2 alone and in combination were compared in blind tests against water alone and against each other to determine various properties the compositions would impart to the hair. Both virgin and bleached hair tresses (Example 4) were used.

In each determination, a composition (2 milliliters) was applied to a tress, the tress combed through once, wrapped on a roller and air dried. Wet hair properties were determined and ranked prior to wrapping, while dry hair properties were determined and ranked after the rolled hair had dried. A composite ranking of results for both virgin and bleached hair is shown below, with a ranking of 1 being the best.

Compositions 1. 0.25 Weight percent polymer of Example 1 in water;
2. 2.5 Weight percent diammonium dithiodiglycolate;
3. 0.25 Weight percent polymer of Example 1 plus 2.5 weight percent diammonium dithiodiglycolate;
4. 0.25 Weight percent polymer of Example 1 plus 1.25 weight percent diammonium dithiodiglycolate;
5. 1.5 Weight percent polymer of Example 1;
6. 2.75 Weight percent polymer of Example 1; and
7. Water control.

| Attributes* | Ranking of Composition** | | | | | | |
|---|---|---|---|---|---|---|---|
| | 1 | 2 | 3 | 4 | 5 | 6 | 7 |
| Dry Hair | | | | | | | |
| Body | 2 | 2 | 1 | 1 | — | — | 3 |
| Combing Ease | — | — | 1 | 1 | 3 | 3 | 2 |
| Feel | — | — | 1 | 1 | 3 | 3 | 2 |
| Appearance | — | — | 1 | 1 | 3 | 3 | 2 |
| Overall Preference | 2 | 2 | 1 | 1 | 4 | 4 | 3 |
| Wet Hair | | | | | | | |
| Combing Ease | 1 | — | 1 | 1 | 1 | 1 | 2 |
| Wrapping Ease and Feel | 2 | — | 1 | 1 | 3 | 4 | — |

*Hair body evaluations are based in large part upon the force required to deform a curl and upon the spring-back of curl from its deformation. Hair feel includes whether harshness was detected to the touch and whether a crust was felt on the hair. Appearance criteria include luster, presence or absence of flakes and fly-away of the hair on drycombing. Wet feel criteria included determinations as to tackiness and slipperiness. The remaining attributes are self-explanatory.
**Each composition had a pH value of between 7.0 and 7.2.

The rankings above demonstrate the superiority of the compositions of this invention (Compositions 3 and 4) over compositions containing equal amounts of the individual components, or an amount of one component equal in weight to the weight of both components. In each instance, the compositions of this invention were ranked as being the best, and in only the case of wet combing ease was another composition equally ranked.

It should be noted that the synergistic effect discussed hereinbefore is particularly illustrated by the rankings for the attributes labeled "Wrapping Ease and Feel." In that determination, the compositions of this invention, Compositions 3 and 4, produced easier wrapping and a better wet feel than did an equal or greater amount of polymer alone (Compositions 1, 5 and 6), thereby demonstrating the synergistic effect of the combination of components.

To examine the film forming properties of the compositions of this invention, ten milliliter samples of each of the above compositions, excluding water alone (No. 7), were placed into petri dishes and allowed to dry. Composition 2, which contained an amount of diammonium dithiodiglycolate within the amounts preferred in this invention, produced a rough, slightly powdery, non-film residue. All of the other compositions produced non-tacky, smooth films, including Composition 3 which contained the same amount of the same dithiopolycarboxylic acid as Composition 2, but also contained a quaternary nitrogen-containing polymer useful herein.

Example 4: Binding of Quaternary Nitrogen Containing Polymer on Different Types of Hair This Example demonstrates the variable binding of the quaternary nitrogen-containing polymer of Examples 1 and 2 on various types of hair. Virgin blonde hair (V) was supplied by DeMeo Brothers of New York and bleached blonde hair (B) was supplied by Alkinco of New York. Waved hair (W) was prepared by treating the virgin hair with a commercial waving lotion for 15 minutes, followed by a water rinse and a 5 minute neutralization with a hydrogen peroxide-containing neutralizer. Bleached/Waved hair (B/W) was prepared by waving the commercially available bleached hair for 3 minutes with a commercial waving lotion, followed by a water rinse and a 3 minute neutralization with a hydrogen peroxide-containing composition. No rollers were used for any of the waved hair.

The four types of hair tresses (V, B, W and B/W) were made into three groups (1, 2 and 3), each of which contained each type of hair. The groups were then treated as follows:

Group (1) deionized water for 5 minutes and rinsed, these tresses served as controls;

Group (2) a prewrap having a pH value of 6.8 and containing 1 weight percent diammonium dithiodiglycolate and 0.25 weight percent of the polymer of Example 1 was applied for 5 minutes and water rinsed; and Group (3) prewrap of Group 2 for 5 minutes, water rinsed, air dried and shampooed.

After the treatments, each of the above groups of hair was soaked in a 0.5 percent solution of Rubine dye for 5 minutes and then thoroughly rinsed with water. The intensity of the color (reddish-purple) left on the hair is an indication of the amount of quaternary polymer which is bound to the hair.

| | Color of Hair After Rubine Dye Treatment | | | |
|---|---|---|---|---|
| | Virgin | Bleached | Waved | Bleached/Waved |
| Group 1 | Blonde | Blonde | Blonde | Pink-Blonde |
| Group 2 | Light-Med. Lav. | Med. Lav. | Med. Lav. | Deep Lav. |
| Group 3 | Light Lav. | Light- | Light- | Deep Lav. |
| | | Med. Lav. | Med. Lav. | |

Med. = medium; Lav. - lavender

These results indicate that the conditioning polymer of the prewrap of Example 1 is bound in a greater amount to hair which has been made porous by chemical treatments. The results also demonstrate substantivity after one shampoo.

Example 5: Take-up of Diammonium Dithioglycolate by Various Types of Hair

Four types of hair were treated for 15 minutes either with a 2.5 weight percent solution of diammonium dithiodiglycolate at pH 7.0 or with deionized water. The hair was centrifuged at 2,800 r.p.m. for 30 minutes to remove excess surface liquid and then dried in a vacuum oven at 110° C. for one hour. The weight gain corresponding to the take-up of the dithiodiglycolic acid salt was then determined by subtracting any weight gain of the control samples from the test sample weight gains.

| Hair Type* | Diammonium Dithiodiglycolate Taken Up (Milligrams/gram of hair) |
|---|---|
| Virgin | 5.2 |
| Waved | 9.8 |
| Bleached | 10.7 |
| Bleached and Waved | 15.4 |

*The hair types of this Example were obtained and/or prepared as were the hair samples of Example 4.

These determinations indicate that hair which is made porous by chemical treatments takes up more of the dithiopolycarboxylic acid salt than hair which is not chemically treated or which has had less severe chemical treatments.

Example 6: Conditioning Efficacy After Multiple Shampoos

Bleached and waved 7-inch tresses were prepared by first bleaching virgin hair from DeMeo Brothers with a commercial bleaching product, followed by shampooing and waving using a commercially available product followed by another shampoo treatment, all following the label instructions. Some of the tresses were treated with the prewrap of Example 1 and then waved without rollers with a commercially available waving lotion containing 2.5 weight percent diammonium dithiodiglycolate and 7 weight percent ammonium thioglycolate and having a pH value of 9.15. The tresses were then rinsed with water, and neutralizing with a composition containing 2.2 weight percent hydrogen peroxide and having a pH value of 3.5. Bleached and waved tresses not treated with prewrap and not additionally waved served as controls.

The tresses were evaluated for a dry combing and fly away control before shampooing, and wet combing after shampooing. Each shampoo treatment utilized an application of a commercially available shampoo followed by rinsing and then another shampoo application and rinse; each such double shampoo application being counted as a single treatment. The tresses were air dried between shampoo treatments. The ratings tabulated below were done blind by experienced workers.

| | Evaluation Ratings | | | | |
|---|---|---|---|---|---|
| | Number of Shampoo Treatments | | | | |
| | 0 | 1 | 2 | 3 | 4 |
| Wet Combing* | | | | | |
| Prewrap | 5 | 5 | 4.5 | 4.5 | 4 |
| Control | 3.5 | 3 | 3 | 3 | 3 |
| Dry Combing* | | | | | |
| Prewrap | 5 | 5 | 5 | 5 | 4.5 |
| Control | 4 | 4 | 3.5 | 3.5 | 3 |
| Fly Away Control** | | | | | |
| Prewrap | 5 | 4.5 | 4.5 | 4.5 | 4 |
| Control | 2 | 2 | 2 | 2 | 2 |

*Wet and Dry Combing Ratings: 5-excellent; 4-good; 3-fair; 2-poor; and 1-very poor.
**Fly Away Control Rating: 5-No fly away; 4-slight fly away; 3-moderate fly away; 2-moderate to excessive fly away; and 1-excessive fly away.

These results demonstrate that the conditioning effect of the compositions of this invention lasts through at least four double shampooings.

Example 7: Binding of Various Quaternary Nitrogen-Containing Polymers

Prewrap conditioning solutions containing 2.5 weight percent diammonium dithiodiglycolate and 0.25 weight percent of one of four quaternary nitrogen-containing polymers in water were prepared according to this invention, each solution having a pH value of 6.5. Virgin white hair (De Meo Brothers) tresses were treated with the prewrap, and that treatment was followed by a 15 minute treatment with a commercially available waving lotion containing 2.5 percent diammonium dithiodiglycolate and 12 percent ammonium thioglycolate having a pH value of 8.9, water rinse, neutralization with a commercially available hydrogen peroxide-containing neutralizer, and a final water rinse.

Thereafter, the tresses were treated with Rubine dye as discussed in Example 4, rinsed and evaluated for dye, and therefore, polymer binding. The tresses were then shampooed twice using double applications of shampoo each time and evaluated again. The results are tabulated below.

| | Color of Hair After Rubine Treatment | |
|---|---|---|
| | After Waving | After two Shampoos |
| Polymer 1 (Note 1) | Deep Lavender | Light Lavender |
| Polymer 2 (Note 5) | Deep Lavender | Light Lavender |
| Polymer 3 (Note 6) | Deep Lavender | Light Lavender |
| Polymer 4 (Note 7) | Deep Lavender | Light Lavender |

(Note 5) Polydiallyldimethylammonium chloride, sold under the designation Merquat-100 by Merck & Company, Inc. and having the CTFA Dictionary name Quaternium-40 was used.
(Note 6) A cationic guar, sold under the designation COSMEDIA GUAR C 261 by Henkel, Inc., and having the CTFA adopted name Guar Hydroxypropyltrimonium Chloride was used.
(Note 7) A copolymer containing acrylamide and N,N—dimethylaminoethyl methacrylate, quaternized with dimethyl sulfate was used. This material has the CTFA Dictionary name Quaternium-39 and is sold under the designation RETEN SPX 1104 by Hercules, Inc.

As the above table shows, all of the quaternary nitrogen containing polymers of the conditioning compositions were bound to the hair after the waving treatment, and all remained bound after two shampoo treatments.

Example 8: Protection From Over Waving

Models having normal and tinted hair were given hair waving treatments using the prewrap of Example 1 and a commercially available waving lotion which contained 2.5 weight percent diammonium dithiodiglycolate. The lotion for normal hair contained 14 weight percent ammonium thioglycolate, while that for tinted hair contained 7 weight percent ammonium thioglycolate. Both waving lotions had pH values of 9.15, and were neutralized with compositions containing 2.2 weight percent hydrogen peroxide in compositions having a pH value of 3.5.

Processing times of 15 minutes (before neutralization) for some models with both types of hair showed good waves for each hair type. No over waving was apparent for models with either hair type even when the processing time was allowed to extend for one hour.

A one hair processing time using a waving lotion or prewrap having no dithiopolycarboxylic acid or salt would normally cause over waving or over processing to the hair. Use of a dithiopolycarboxylic acid or its salts in the waving lotion would retard this over waving to some degree. The use of a dithiopolycarboxylic acid or its salt in both the prewrap and waving lotion entirely eliminated over waving, while allowing a good wave to be obtained.

Example 9: Wrapping of Hair Treated With Relatively Small Molecule vs. Polymeric Quaternary Nitrogen-Containing Conditioners Eight compositions having pH values of 6.5 to 7.0 were prepared as listed below and applied in equal amounts (2 milliliters, each) to virgin hair tresses (Example 4). The compositions were combed once through the hair, the hair was wrapped on rollers and allowed to air dry. A ninth aqueous solution with no additive served as control.

| Compositions (Weight % Active) | |
|---|---|
| Polymer of Example 1 | Small Molecule* |
| 0.25 | 0.25 |
| 0.50 | 0.50 |
| 1.00 | 1.00 |
| 2.00 | 2.00 |

*The relatively small molecule used was a 50% active solution of oleyl dimethyl benzyl ammonium chloride, a well known relatively small molecule conditioner.

All of the hair treated with a polymer of Example 1 felt slippery and was difficult to wrap on rollers. Increasing polymer concentrations caused the hair to be increasingly more slippery, making wrapping more and more difficult. None of the hair treated with the relatively small molecule conditioner was slippery, and the hair so treated wrapped on rollers in a manner similar to hair treated only with water.

As seen from the results in Example 3, above, the use of 2.5 or 1.25 weight percent diammonium dithioglycolate in compositions which also contained 0.25 weight percent of the polymer of Example 1 and of this Example produced a composition providing the best wet feel and wrapping qualities of those tested; i.e. the compositions did not produce an objectionable slippery feel to the wet hair and were not difficult to wrap on hair.

In another demonstration, the above compositions were applied to bleached hair tresses (Example 4) and the hair was treated as described above in the Example.

After drying, each tress was washed with a generous amount of a commercial shampoo and the ease of detangling rated thereafter. In each instance, tresses treated with the above polymeric conditioner were easy to detangle, while those tresses treated with the relatively small molecule conditioner was difficult to detangle, thereby demonstrating the relative substantiveness after shampooing of each conditioning agent.

Example 10: Comparative Tensile Strength Determinations

The break (tensile) strength of dry hair treated as discussed hereinafter was determined using an Instron tensile testing machine. A single lot of virgin hair tresses (DeMeo Brothers) was used with twelve fibers being broken for each determination. The tensile strength determinations and denier measurements were performed at 52% relative humidity and 72° F. after equilibration of the hair fibers under those conditions.

The put-on, leave-on conditioner of Example 2 was used for these determinations along with a commercially available shampoo and waving product having a pH value of 9.4 and containing 8.9 weight percent ammonium thioglycolate. Neither the shampoo nor the waving product contained a conditioning agent. Package directions were followed for use of the commercial products using amounts appropriate to tresses containing about two grams of hair. A generous amount of the conditioner of Example 2 was applied to the appropriate tresses and combed through each tress to distribute it on to the hair fibers and to eliminate any conditioner which was not absorbed by the tress. The steps of the treatment sequence are shown below in the order listed for each treatment condition.

Treatment Conditions

1. Wave only;
2. Conditioner, wave, conditioner;
3. Wave, shampoo;
4. Conditioner, wave, conditioner, shampoo, conditioner; and
5. Wave, shampoo, conditioner.

| Treatment | Hair Break Strength After Various Treatments Mean Tensile Strength (grams/denier) |
|---|---|
| 1 | 1.476 |
| 2 | 2.175 |
| 3 | 1.919 |
| 4 | 2.084 |
| 5 | 2.048 |

As can be seen from the above Table, treatment of waved hair with a composition of this invention improved the tensile strength of the hair thereby demonstrating the protective properties of these compositions. The difference in tensile strength shown above between Treatments 1 and 2 was statistically significant at at least the 95% confidence level using a Student's test. It is believed that the actual difference in tensile strengths between treatments 1 and 2 may actually be larger than that shown because the use of the conditioner is known to add weight to the fiber thereby raising the fiber's denier and the denominator of the grams per denier fraction.

The value for the mean tensile strength of waved and shampooed hair (Treatment 3) appears to be anomalously high, although part of the magnitude of the value may be due to a weight and denier lowering effect on the fibers caused by elimination of any waving lotion residue left in the hair. Regardless of this seemingly, anomolously high value, the data of the above Table indicate that there is an improvement in mean hair tensile strength when the conditioner of Example 2 is applied to waved hair which has also been shampooed (Treatments 4 and 5) as compared to waved hair alone (Treatment 1) and as compared to waved and shampooed hair (Treatment 3). The improvements in mean hair tensile strength of Treatments 4 and 5 compared to Treatment 1 were each statistically significant at at least the 95% confidence level using the Student's test.

The present invention has been described with respect to the preferred embodiments of the invention. It will be clear to those skilled in the art that modifications and/or variations of the disclosed methods and compositions may be made without departing from the scope of the invention set forth herein. The invention is defined by the claims which follow.

What is claimed is:

1. A composition for conditioning hair comprising water having dissolved therein about 0.05 to about 5 weight percent of a quaternary nitrogen-containing polymer having a molecular weight between about 10,000 and about 10,000,000 and about 0.5 to about 10 weight percent of a water-soluble, disulfide-containing polycarboxylic acid or salt thereof, said composition having a pH value at 80° F. from about 4 to about 9.

2. The composition of claim 1 wherein said polymer is present at about 0.1 to about 2 weight percent.

3. The composition of claim 1 wherein said polymer is selected from the group consisting of a homopolymerized diallyldimethyl ammonium salt, a diallydimethylammonium salt copolymerized with acrylamide, a cationic hydroxyethyl cellulose derivative having a chain of anhydroglucose units with substituent groups pendant therefrom and spaced along said chain, said hydroxyethyl cellulose derivative containing a plurality of quaternary nitrogen-containing groups, having from zero to 3 moles of said nitrogen-containing groups per anhydroglucose unit, a cationic guar of mannopyranosyl and qalactopyranosyl units having 3-trimethylammonium-2-hydroxypropyl groups bonded to said mannopyranosyl and qalactopyranosyl units, a copolymer comprised of about 80 weight percent vinyl pyrrolidone units and about 20 weight percent N,N-dimethyl-aminoethyl methacrylate quaternized with dimethyl sulfate, and copolymers of acrylamide and N,N-dimethylaminoethyl methacrylate quaternized with dimethyl sulfate.

4. The composition of claim 1 wherein said disulfide-containing dicarboxylic acid is present at about 1 to about 5 weight percent.

5. The composition of claim 1 wherein said disulfide-containing polycarboxylic acid is selected from the group consisting of dithiodiglycolic acid, 3,3-dithiodipropionic acid, cystine, dithiodilactic acid, and dithiodisuccinic acid.

6. A composition for conditioning hair comprising water having dissolved therein about 0.1 to about 2 weight percent of a quaternary nitrogen-containing polymer having a molecular weight between about 100,000 and about 4,000,000, said polymer being selected from the group consisting of a homopolymerized diallyldimethylammonium salt, a diallyldimethylammonium salt copolymerized with acrylamide, a cationic hydroxyethyl cellulose derivative having a chain of anhydroglucose units with substituent groups pendant therefrom and spaced along said chain, said hydroxyethyl cellulose derivative containing a plurality of quaternary nitrogen-containing groups, having from zero to 3 moles of said nitrogen-containing groups per anhydroglucose unit, a cationic guar of mannopyranosyl and galactopyranosyl units having 3-trimethylammonium-2-hydroxypropyl groups bonded to said mannopyranosyl and galactopyranosyl units, a copolymer comprised of about 80 weight percent polymerized N-vinyl pyrrolidone and about 20 weight percent N,N-dimethylaminoethyl methacrylate quaternized with dimethyl sulfate, and copolymers of acrylamide and N,N-dimethylaminoethyl methacrylate quaternized with dimethyl sulfate, and about 1 to about 5 weight percent of a water-soluble disulfide-containing dicarboxylic acid or salt thereof selected from the group consisting of dithiodiglycolic acid, 3,3-dithiodipropionic acid, and dithiodilactic acid and cystine, said composition having a pH value measured at 80° F. of about 5 to about 8.

7. The composition of claim 6 wherein said disulfide-containing dicarboxylic acid is present as an alkali metal or ammonium salt.

8. A composition for conditioning hair comprising water having dissolved therein about 0.1 to about 1 weight percent of a cationic hydroxyethyl cellulose ether derivative having an average molecular weight between about 300,000 and 1,000,000 and a chain of anhydroglucose units with substituent groups pendant therefrom and spaced along said chain, said hydroxyethyl cellulose derivative containing a plurality of quaternary nitrogen-containing groups, having from zero to 3 moles of said nitrogen-containing groups per anhydroglucose unit, and about 1 to about 5 weight percent diammonium dithiodiglycolate, said composition having a pH value at 80° F. of about 6.5 to about 8.

9. A process for treating hair whose configuration is to be altered including the steps of:
applying the composition of claim 1 to the hair;
distributing said composition substantially evenly throughout said hair; and
altering the configuration of the hair while the hair is at least partially damp.

10. The process of claim 9 wherein said hair is wound on rollers while at least partially damp, and then dried to alter the configuration of said hair.

11. A process for treating hair whose configuration is to be altered including the steps of:
applying the composition of claim 6 to the hair;
distributing said composition substantially evenly throughout said hair; and
altering the configuration of the hair by winding said hair upon rollers while said hair is at least partially damp.

12. The process of claim 11 wherein said configuration alteration is a permanent wave.

13. A process for treating hair to be waved by selectively conditioning and providing portions of the hair fibers with a preselected propensity for waving including the steps of:
dividing the hair to be waved into a plurality of sections;
applying the composition of claim 8 to a first hair section;
distributing said composition substantially evenly throughout said first hair section;
winding said first hair section on a roller while said hair is at least partially damp;
repeating said applying, distributing and winding steps on each remaining section until all of said hair to be waved is wound on rollers; and
waving said wound hair.

14. In the process of waving human hair wherein said hair is treated with a prewrap solution, said prewrap solution-treated hair is wrapped on rollers while the hair is at least partially damp, treated with a thiol-containing waving agent to break hair disulfide bonds, and said broken disulfide bonds are realigned, and reformed with an oxidizing agent, the improvement wherein said prewrap solution is comprised of the composition of claim 1.

15. In the process of waving human hair wherein said hair is treated with a prewrap solution, said prewrap solution-treated hair is wrapped on rollers while the hair is at least partially damp, treated with a thiol waving agent to break hair disulfide bonds, and said broken disulfide bonds are realigned, and reformed with an oxidizing agent, the improvement wherein said prewrap solution is comprised of the composition of claim 6.

16. In the process of waving human hair wherein said hair is treated with a prewrap solution, said prewrap solution-treated hair is wrapped on rollers while the hair is at least partially damp, treated with a thiol waving agent to break hair disulfide bonds, and said broken disulfide bonds are realigned, and reformed with an oxidizing agent, the improvement wherein said prewrap solution is comprised of the composition of claim 8.

* * * * *